United States Patent [19]

Wroblowsky et al.

[11] Patent Number: 5,703,260
[45] Date of Patent: Dec. 30, 1997

[54] PROCESS FOR THE PREPARATION OF ALKOXYTRIAZOLINONES

[75] Inventors: Heinz-Jürgen Wroblowsky, Langenfeld; Klaus König, Odenthal, both of Germany

[73] Assignee: Bayer Aktiengesellschaft, Leverkusen, Germany

[21] Appl. No.: 714,668

[22] Filed: Sep. 16, 1996

Related U.S. Application Data

[62] Division of Ser. No. 528,584, Sep. 15, 1995, Pat. No. 5,594,147.

[30] Foreign Application Priority Data

Sep. 23, 1994 [DE] Germany .................. 44 33 966.6

[51] Int. Cl.$^6$ .................................................. C07C 281/06
[52] U.S. Cl. .................................................................. 558/8
[58] Field of Search ................................................... 558/8

[56] References Cited

U.S. PATENT DOCUMENTS 5,356,865 10/1994 Muller et al. ............................ 504/273
5,488,028 1/1996 Haas et al. ............................... 504/193

FOREIGN PATENT DOCUMENTS 0447646  4/1992  European Pat. Off. .
0507171 10/1992  European Pat. Off. .

OTHER PUBLICATIONS

J. Indian Chem. Soc.; vol. 6(1929), pp. 565–575.
J. Chem. Soc. Perkin I 1973, pp. 2644–2646.
Arch. Pharm. vol. 307(1974), pp. 889–891.
Chemical Abstracts vol. 82 (1975): 86060x.
F. Arndt et al., Rev. Fac. Sci. Istanbul vol. 13A (1948), pp. 127–144 (in German).
Chemical Abstracts vol. 42 (1948): 8190d.

*Primary Examiner*—Richard L. Raymond
*Attorney, Agent, or Firm*—Sprung Kramer Schaefer & Briscoe

[57] ABSTRACT

Alkoxytriazolinones of the general formula (I),

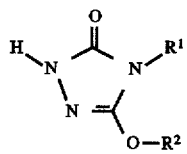

in which
R$^1$ represents hydrogen, or represents in each case optionally substituted alkyl, alkenyl, alkinyl, cycloalkyl, cycloalkylalkyl, aryl or arylalkyl, and
R$^2$ represents in each case optionally substituted alkyl, alkenyl, alkinyl, cycloalkyl, cycloalkylalkyl, ary or arylalkyl, (which can be used as intermediates for the preparation of herbicidal active compounds) are obtained in very good yields and in high purity by reacting imino(thio)carbonic esters (II) with alkoxyethyl carbazinates (III)

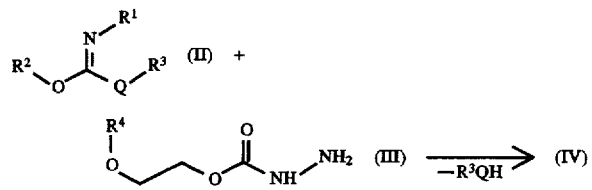

in which Q represents O or S, R$^3$ represents (for example) alkyl, aryl or aralkyl and R$^4$ represents (for example) alkyl, at –20° C. to +150° C. (1st step) and subjecting the new semicarbazide derivatives (IV)

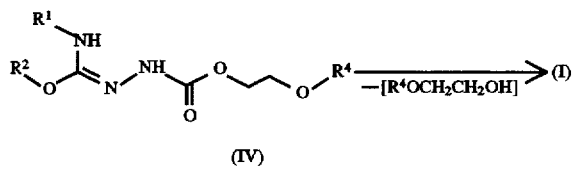

which are formed with elimination of R$^3$—QH, if appropriate after intermediate isolation, to a cyclizing condensation reaction at 0° C. to 200° C., without the addition of a base, advantageously under reduced pressure, with the elimination of alkoxyethanols (2nd step).

4 Claims, No Drawings

PROCESS FOR THE PREPARATION OF ALKOXYTRIAZOLINONES

This is a division of application Ser. No. 08/528,584, filed on Sep. 15, 1995 now U.S. Pat. No. 5,594,174.

The invention relates to a new process for the preparation of alkoxytriazolinones, most of which are known and which can be used as intermediates for the preparation of agrochemical active compounds, it also being possible for the process to be carried out on an industrial scale.

Alkoxytriazolinones and a plurality of methods for their preparation are already known (cf. J. Indian Chem. Soc. 6 (1929), 565–575; J. Chem. Soc. Perkin I 1973, 2644–2646; Arch. Pharm. 307 (1974), 889–891; EP-A477646; EP-A507171). However, these known synthetic methods give alkoxytriazolinones only in highly unsatisfactory yields.

It is furthermore known to form 5-methoxy-4-methyl-2,4-dihydro-3H-1,2,4-triazol-3-one by methylating urazole or 4-methylurazole with diazomethane ($CH_2N_2$) [cf. F. Arndt et al, Rev. Fac. Sci. Istanbul 13A, pp. 127 to 144 (1948)]; while this method affords high yields of the triazolinone, it cannot be carried out on an industrial scale.

It has now been found that alkoxytriazolinones of the general formula (I)

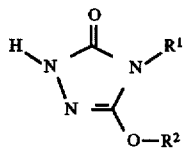

in which $R^1$ represents hydrogen, or represents in each case optionally substituted alkyl, alkenyl, alkinyl, cycloalkyl, cycloalkylalkyl, aryl or arylalkyl and $R^2$ represents in each case optionally substituted alkyl, alkenyl, alkinyl, cycloalkyl, cycloalkylalkyl, aryl or arylalkyl, are obtained in very good yields and in high purity when imino(thio)carbonic diesters of the general formula (II)

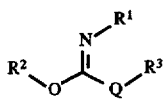

in which $R^1$ and $R^2$ have the abovementioned meanings,

Q represents oxygen or sulphur and $R^3$ represents in each case optionally substituted alkyl, aryl or arylalkyl, are reacted with alkoxyethyl carbazinates of the general formula (III)

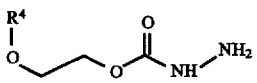

in which $R^4$ represents optionally substituted alkyl, if appropriate in the presence of a reaction auxiliary and if appropriate in the presence of a diluent at temperatures between −20° C. and +150° C. ("first reaction step") and the semicarbazide derivatives formed in this process of the general formula (IV)

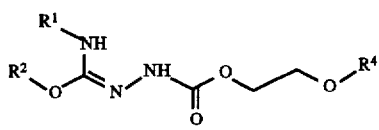

in which $R^1$, $R^2$ and $R^4$ have the abovementioned meanings, and/or the corresponding tautomeric compounds are subjected to a cyclizing condensation reaction, at temperatures between 0° C. and 200° C., if appropriate after intermediate isolation, and if appropriate in the presence of a diluent, if appropriate under reduced pressure ("second reaction step").

Surprisingly, the alkoxytriazolinones of the general formula (I) can be obtained in considerably higher yields by the process according to the invention than by most of the known synthetic methods.

Compared with the "diazomethane method" (F. Arndt et al., 1. c.) the decisive advantage of the process according to the invention is that it can also be carried out on an industrial scale.

In contrast to the known process, in which phenol is formed as coupling product—$R^4$ represents phenyl (cf. EP-A 507171, Examples II-1 and II-2)—the second step of the process according to the invention can also be carried out in a problem-free manner—without an addition of a base—with the elimination of alkoxyethanols, which can be recovered in a considerably more simple and less complicated fashion than in the case of phenol.

A particular advantage of the process according to the invention is the fact that many of the carbazinic esters of the formula (III) to be used are liquid at room temperature and at the reaction temperature, thus allowing the use of a diluent in many cases simply to be dispensed with.

The process according to the invention therefore represents a valuable enrichment of the prior art.

The invention preferably relates to the preparation of compounds of the formula (I) in which $R^1$ represents hydrogen, or represents alkyl, alkenyl or alkinyl, each of which has up to 6 carbon atoms and each of which is optionally substituted by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or ($C_1$–$C_4$-alkoxy)-carbonyl, and $R^2$ represents alkyl, alkenyl or alkinyl, each of which has up to 6 carbon atoms and each of which is optionally substituted by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or ($C_1$–$C_4$-alkoxy)-carbonyl.

The invention particularly relates to the preparation of compounds of the formula (I) in which $R^1$ represents methyl, ethyl, n- or i- propyl or n-, i-, s- or t-butyl, each of which is optionally substituted by fluorine, chlorine, bromine, methoxy or ethoxy, or represents propenyl, butenyl, propionyl or butinyl, each of which is optionally substituted by fluorine and/or chlorine, or represents cyclopropyl $_1$–$C_4$ or cyclopropylmethyl, each of which is optionally substituted by fluorine, chlorine, methyl or ethyl, or represents phenyl or benzyl, each of which is optionally substituted by fluorine, chlorine, bromine, methyl, ethyl, trifluoromethyl, methoxy, ethoxy, difluoromethoxy or trifluoromethoxy, and $R^2$ represents methyl, ethyl, n- or i- propyl or n-, i-, s- or t-butyl, each of which is optionally substituted by fluorine, chlorine, bromine, methoxy or ethoxy, or represents propenyl, butenyl, propinyl or butinyl, each of which is optionally substituted by fluorine and/or chlorine or represents cyclopropyl or cyclopropylmethyl, each of which is optionally substituted by fluorine, chlorine, bromine, methyl or ethyl, or represents phenyl or benzyl, each of which is optionally substituted by fluorine, chlorine, bromine, methyl, ethyl, trifluoromethyl, methoxy, ethoxy, difluoromethoxy or trifluoromethoxy.

If, for example, dimethyl methylimino-carbonate and 2-methoxyethyl carbazinate are used as starting substances, the course of the reaction in the process according to the invention can be outlined by the following equation:

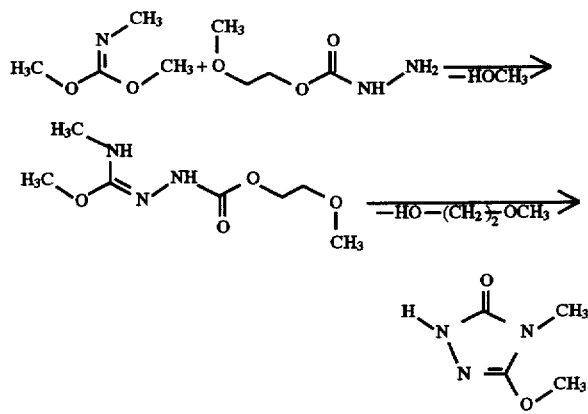

Formula (II) provides a general definition of the imino (thio)carbonic diesters to be used as starting substances in the process according to the invention for the preparation of the compounds of the general formula (I). In formula (II), $R^1$ and $R^2$ preferably, or in particular, have those meanings which have already been mentioned above in connection with the description of the compounds of the formula (I) as preferred or as particularly preferred, for $R^1$ and $R^2$; $R^3$ preferably represents $C_1$–$C_4$-alkyl, phenyl or benzyl, optionally substituted-by hydroxy, carboxyl, $C_1$–$C_4$-alkoxy, $C_1$–$C_4$-alkoxy-carbonyl, phenoxy or benzyloxy, in particular methyl, ethyl, methoxyethyl or ethoxyethyl.

The starting substances of the formula (II) are known and/or can be prepared by processes known per se (cf. Chem. Ber. 120 (1987), 339–344; preparation examples).

Formula (III) provides a general definition of the alkoxyethyl carbazinates furthermore to be used as starting substances in the process according to the invention. In formula (III), $R^4$ preferably represents $C_1$–$C_4$-alkyl, optionally substituted by $C_1$–$C_4$-alkoxy, phenoxy or benzyloxy, and in particular represents methyl, ethyl, 2-methoxyethyl or 2-ethoxyethyl.

The starting substances of the formula (III) are known and/or can be prepared by processes known per se (of. Chem. Ber. 114 (1981), 2001–2018; preparation examples).

Formula (IV) provides a general definition of the semicarbazide derivatives obtained as intermediates in the process according to the invention for the preparation of the compounds of the general formula (I). In Formula (IV), $R^1$ and $R^2$ preferably, or in particular, have those meanings which have already been mentioned above in connection with the the description of the compounds of the formula (I) as being preferred or particularly preferred for $R^1$ and $R^2$; $R^4$ preferably represents $C_1$–$C_4$-alkyl which is optionally substituted by $C_1$–$C_4$-alkoxy, phenoxy or benzyloxy, in particular methyl, ethyl, 2-methoxyethyl or 2-ethoxyethyl.

The intermediates of the formula (IV) were hitherto unknown from the literature; being new substances, they are also a subject of the present application.

Diluents which are suitable for carrying out the process according to the invention are (in both reaction steps) the customary organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methyl-pyrrolidone or hexamethylphosphoric triamide; esters such as methyl acetate or ethyl acetate; sulphoxides such as dimethyl sulphoxide; alcohols such as methanol, ethanol, n- or i-propanol, ethylene glycol monomethyl ether, ethylene glycol monoethyl ether, diethylene glycol monomethyl ether, diethylene glycol monoethyl ether: mixtures of these with water, or pure water.

However, the process according to the invention can also be carried out successfully without the use of one of the abovementioned diluents.

The first step of the process according to the invention is preferably carried out in the presence of a suitable reaction auxiliary. Suitable reaction auxiliaries are preferably protonic acids such as, for example, hydrochloric acid, sulphuric acid, phosphoric acid, carbonic acid, acetic acid, propionic acid, pivalic acid, methanesulphonic acid, benzoic acid, benzenesulphonic acid and p-toluenesulphoric acid, but, if appropriate, also acidic ion exchangers.

Particularly preferred reaction auxiliaries in the first steps of the process according to the invention are pivalic acid, (aqueous) hydrochloric acid and acetic acid.

When carrying out the first step of the process according to the invention, the reaction temperatures can be varied within a substantial range. In general, the process is carried out at temperatures between –20° C. and +150° C., preferably at temperatures between 0° C. and 120° C., in particular at temperatures between 10° C. and 100° C.

When carrying out the second step of the process according to the invention, the reaction temperatures can be varied within a substantial range. In general, the process is carried out at temperatures between 0° C. and 200° C., preferably at temperatures between 50° C. and 180° C.

The first step of the process according to the invention is generally carried out under atmospheric pressure. However, it is also possible to carry out the process under elevated or reduced pressure, in general between 0.1 bar and 10 bar.

The second step of the process according to the invention is generally carried out under reduced pressure, preferably between 0.001 and 100 mbar, in particular between 0.01 and 50 mbar.

For carrying out the process according to the invention for the preparation of the compounds of the formula (I), 0.5 to 1.2 mol, preferably 0.8 to 1.1 mol, of alkoxyethyl carbazinates of the formula (III) and, if appropriate, 0.001 to 2.0 mol, preferably 0.01 to 1.0 mol, of reaction auxiliary are generally employed per mole of imino(thio)carbonic diesters of the formula (II).

In a preferred embodiment of the process according to the invention, the starting substances of the formula (II) and of the formula (III) and, if appropriate, a reaction auxiliary are mixed—if appropriate in a suitable diluent—and stirred at the temperature required until virtually no starting material is present. The intermediate of the formula (IV) can then be isolated in the customary manner. However, the intermediate of the formula (IV) can also be stirred—if appropriate dissolved in one of the abovementioned diluents—at the temperature required for the cyclizing condensation until the reaction has ended, without intermediate isolation, and subsequently isolated by distillation, preferably under reduced pressure.

The compounds of the formula (I) to be prepared by the process according to the invention can be used as intermediates for the preparation of herbicidally active compounds (cf. EP-A 477646 and EP-A 507171).

Preparation examples

Example 1

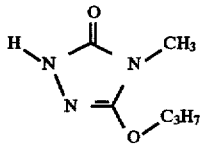

A mixture of 888 g (6.0 mol) of 2-ethoxyethyl carbazinate and 954 g (6.0 mol) of di-n-propyl methyliminocarbonate is heated for 17 hours at 80° C. and for a further 2 hours at 100° C. As the pressure goes down (end pressure 15 mbar), first propanol and already eliminated ethoxyethanol are distilled off, the further reaction being accelerated by raising the temperature to 120° C. As the distillation subsides under these conditions, a fresh, ice-cold receiving vessel is attached for collecting the distillate under atmospheric pressure, the cooling water of the condenser is heated to 80° C., and the further distillation is carried out under an oil-pump vacuum. The bottom temperature is then gradually raised to 150° C. to 170° C. In the course of 2 hours, 823 g of a pale yellow distillate are obtained, which gradually solidifies as crystals and, according to GC analysis, contains 87.2% of 4-methyl-5-propoxy-2,4-dihydro-3H-1,2,4-triazol-3-one. Yield: 76% of theory.

Redistillation gives a 98% pure product of melting point 67° C.

Example 2

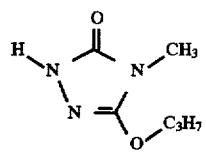

A solution of 1.0 g (0.01 mol) of pivalic acid in 1.5 ml of n-propanol is added at approximately 10° C. to a mixture of 296 g (2.0 mol) of 2-ethoxyethyl carbazinate and 3 18 o (2.0 mol) of di-n-propyl methyliminocarbonate, and the mixture is stirred for 4 hours at 10° C. to 20° C. After an additional 1.0 g of pivalic acid has been added, the mixture is stirred for another 12 hours at 20° C. to 25° C. Propanol is subsequently distilled off at a bottom temperature of approximately 100° C. and a pressure of 15 mbar. Approximately 170 g of ethoxyethanol are then distilled off in the course of approximately 90 minutes at a bottom temperature of approximately 140° C. and a pressure of 15 mbar. When the distillation subsides under these conditions, a fresh, ice-cooled receiving vessel is attached for collecting the distillate under atmospheric pressure, the cooling water of the condenser is heated to 80° C., and the further distillation is carried out under an oil-pump vacuum. The bottom temperature is then gradually raised to 140° C. to 180° C.; the still temperature is approximately 135° C. and the pressure approximately 1 mbar.

275 g of a distillate which, according to GC analysis, contains 95.3% of 4-methyl-5-propoxy-2,4-dihydro-3H-1,2,4-triazol-3-one are obtained. Yield: 83.5% of theory.

Example 3

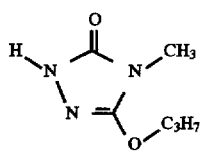

Carbon dioxide is passed for 12 hours at 40° C. into a mixture of 37.7 g (0.239 mol) of 2-ethoxyethyl carbazinate, 38 g (0.239 mol) of O-n-propyl S-methyl methyliminothiocarbonate, 50 ml of n-propanol and 4.5 g of water. Evaporation and distillation in vacuo (oil pump) gives 40 g of crude distillate whose content of the desired 4-methyl-5-propoxy-2,4-dihydro-3H-1,2,4-triazol-3-one amounts to 66.1%. Yield: 67.4% of theory.

Example 4

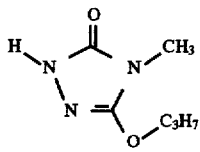

One equivalent of pivalic acid is added at 0° C. to a mixture of 37.7 g (0.239 mol) of 2-ethoxyethyl carbazinate, 38 g (0.239 mol) of O-n-propyl S-methyl methyliminothiocarbonate and 50 ml of n-propanol. Stirring is continued for 2 hours at room temperature, the mixture is concentrated under a water pump vacuum and the residue subsequently distilled under an oil-pump vacuum. 39 g of a crude distillate whose content of the desired 4-methyl-5-propoxy-2,4-dihydro-3H-1,2,4-triazol-3-one amounts to 80.6% are obtained. Yield: 80.1% of theory.

Example 5

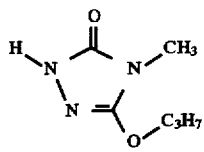

74 g (0.5 mol) of 2-ethoxyethyl carbazinate are introduced into 150 ml of n-propanol, and a solution of 18.3 g (0.5 mol) of hydrogen chloride gas in 98 g of n-propanol is added with ice-cooling. 95.5 g (0.5 mol) of O-n-propyl S-(2-methoxyethyl) methyliminothiocarbonate are then added dropwise in the course of 30 minutes with further ice-cooling. After a further hour at 20° C., the mixture is neutralized by adding 0.5 mol of 30% strength methanolic sodium methanolate solution, and the mixture is then concentrated in vacuo. The product is removed from the sodium chloride formed by a distillation starting at 120° C./1 mbar, 53.1 g of a crude distillate being obtained whose content of the desired triazolinone of the above formula amounts to 92.2%. Yield: 62.4% of theory.

Example 6

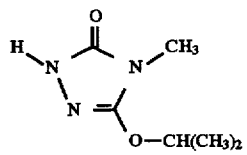

A mixture of 148 g (1 mol) of O-isopropyl S-methyl methyliminothiocarbonate and 147 g (1 mol) of 2-ethoxyethyl carbazinate is heated for 5 hours at 120° C. The evolution of gas then ceases. The mixture is then concentrated at 20 mbar and the residue subsequently distilled over a short column at 1 mbar. This gives 103 g of a crude distillate whose content of the desired product amounts to 62.1% (yield: 40.7% of theory). After recrystallization from toluene, the 4-methyl-5-isopropoxy-2,4-dihydro-3H-1,2,4-triazol-3-one is obtained as a colourless solid of melting point 140° to 141° C.

Example 7

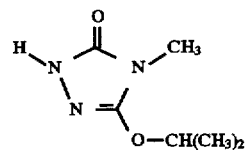

182 g (1.23 mol) of 2-ethoxyethyl carbazinate are mixed with 161 g (1.23 mol) of O-methyl O-i-propyl methyliminocarbonate and, after 3 g of pivalic acid have been added, the mixture is stirred for 8 hours at 20° C. and a further hour at 40° C. It is then concentrated under a water pump vacuum at a bottom temperature of not more than 100° C. and then distilled under an oil-pump vacuum at a bottom temperature of not more than 180° C. The distillate is recrystallized from toluene.

164 g (85% of theory) of 4-methyl-5 -i-propoxy-2,4-dihydro-3H-1,2,4-triazol-3 -one of melting point 142° C. are obtained.

Example 8

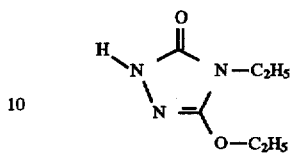

Analogously to Example 2, by reacting equimolar amounts of 2-ethoxyethyl carbazinate and diethyl ethyliminocarbonate in the presence of pivalic acid (2 mol-% and subjecting the intermediate thereby formed to a cyclizing condensation reaction there is obtained 5-ethoxy-4-ethyl-2,4-dihydro-3H-1,2,4-triazol-3-one (yield: 85% of theory, after distillation), of m.p. 115° C. (recrystallized from toluene).

Example 9

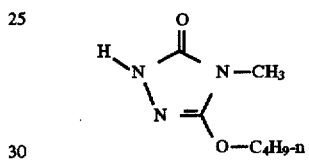

Analogously to Examples 2 and 8, there is obtained 5-n-butoxy-4-methyl-2,4-dihydro-3H-1,2,4-triazol-3-on (yield: 76% of theory) of m.p. 77° C. (recrystallized from cyclohexane/toluene, 4:1 by volume).
Starting substances of the formula (III)

Example (III-1)

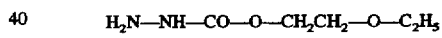

$H_2N-NH-CO-O-CH_2CH_2-O-C_2H_5$ 1125 g (22.5 mol) of hydrazine hydrate are added dropwise in the course of 2 hours to 4635 g (22.5 mol) of bis-(2-ethoxyethyl) carbonate, and the mixture is then stirred for 2 hours at 60° C. and for a further hour at 80° C. Water and ethoxyethanol are then distilled off at 15 mbar, and the crude product which remains is purified by distillation under an oil pump vacuum.

3164 g (95% of theory) of 2-ethoxyethyl carbazinate of boiling point 99° C. (at 0.15 mbar) are obtained.

Other substances which can be prepared analogously are, for example, 2-methoxyethyl carbazinate, 2-propoxyethyl carbazinate, 2-butoxyethyl carbazinate, 2-(2-methoxyethoxy)ethyl carbazinate, 2-(2-ethoxyethoxy)ethyl carbazinate and 2-benzyloxyethyl carbazinate.

We claim:
1. A semicarbazide derivative of the formula

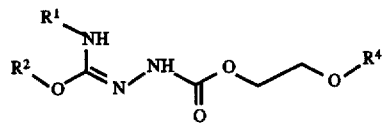

(IV)

in which
$R^1$ represents hydrogen, or represents alkyl, alkenyl or alkinyl, each of which has up to 6 carbon atoms and each of which is optionally substitued by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl, and $R^2$ represents alkyl, alkenyl or alkinyl, each of which has up to 6 carbon atoms and each of which is optionally substituted by halogen or $C_1$–$C_4$-alkoxy, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen or $C_1$–$C_4$-alkyl, or represents aryl or arylalkyl, each of which has 6 or 10 carbon atoms in the aryl moiety and, if appropriate, 1 to 4 carbon atoms in the alkyl moiety and each of which is optionally substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl, $R^4$ represents $C_1$–$C_4$-alkyl which is optionally substituted by $C_1$–$C_4$ alkoxy, phenoxy, or benzyloxy, or a tautomeric compound thereof.

2. A compound according to claim 1, wherein $R^4$ is methyl, ethyl, 2-methoxyethyl or 2-ethoxyethyl.

3. A compound according to claim 1, wherein $R^1$ is methyl, $R^2$ is methyl, and $R^4$ is methyl or ethyl.

4. A compound according to claim 1, wherein $R^1$ is methyl, $R^2$ is n-propyl and $R^4$ is methyl or ethyl.

* * * * *